United States Patent [19]

Bergersen

[11] 4,330,272
[45] May 18, 1982

[54] MEANS FOR ATTACHING A HEADGEAR TO A POSITIONER

[76] Inventor: Earl O. Bergersen, 950 Linden Ave., Winnetka, Ill. 60093

[21] Appl. No.: 127,051

[22] Filed: Mar. 4, 1980

[51] Int. Cl.³ .............................................. A61C 3/00
[52] U.S. Cl. ........................................... 433/5; 433/6
[58] Field of Search ........................................ 433/5, 6

[56] References Cited

U.S. PATENT DOCUMENTS

| 2,822,612 | 2/1958 | Strickler | 433/5 |
| 2,880,509 | 4/1959 | Strickler | 433/5 |
| 2,983,046 | 5/1961 | Jenkins | 433/5 |
| 3,087,245 | 4/1963 | Asher | 433/5 |
| 3,311,977 | 4/1967 | Drake | 433/5 |
| 3,638,313 | 2/1972 | Cervera | 433/5 |
| 3,814,087 | 6/1974 | Heikes | 433/5 |
| 3,898,736 | 8/1975 | Bergersen | 433/6 |
| 3,903,604 | 9/1975 | Snead | 433/5 |
| 3,918,159 | 11/1975 | Andrews | 433/5 |
| 4,212,637 | 7/1980 | Dougherty et al. | 433/5 |

FOREIGN PATENT DOCUMENTS 2348728 12/1974 Fed. Rep. of Germany .......... 433/6

OTHER PUBLICATIONS

"OPA" ad, Hoffman, p. 44, 1978.
"C-Modeler" ad, Cervera, pp. 62, 63, 1977.

Primary Examiner—Gene Mancene
Assistant Examiner—John J. Wilson
Attorney, Agent, or Firm—Hill, Van Santen, Steadman, Chiara & Simpson

[57] ABSTRACT

An orthodontic appliance having a cervical or high pull headgear apparatus attached to a tooth positioner is provided. The positioner, either preformed or custom made and the headgear portion are provided with a secure, yet detachable connection to allow the headgear to be used as a temporary supplement to the tooth positioner and thus provide therapeutic flexibility. Accordingly, the headgear portion may be attached by having wires received in tubes or by hooks, both of which are attached to the outside of the tooth positioner, or by inserting the wires into holes provided in the positioner. The headgear apparatus may thereby be utilized in a number of patients without the requirement for extensive individualized fittings.

10 Claims, 16 Drawing Figures

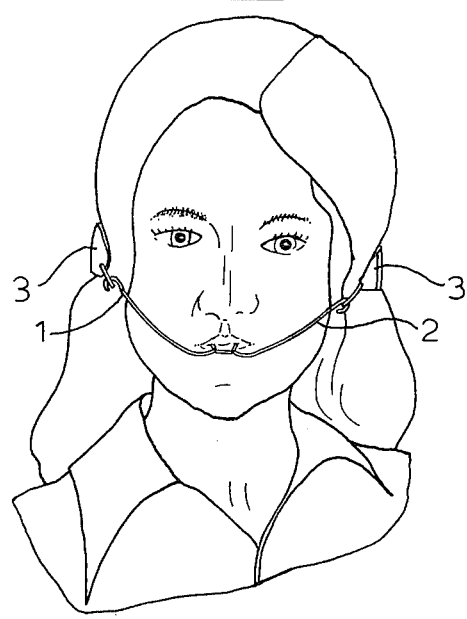
FIG. 1
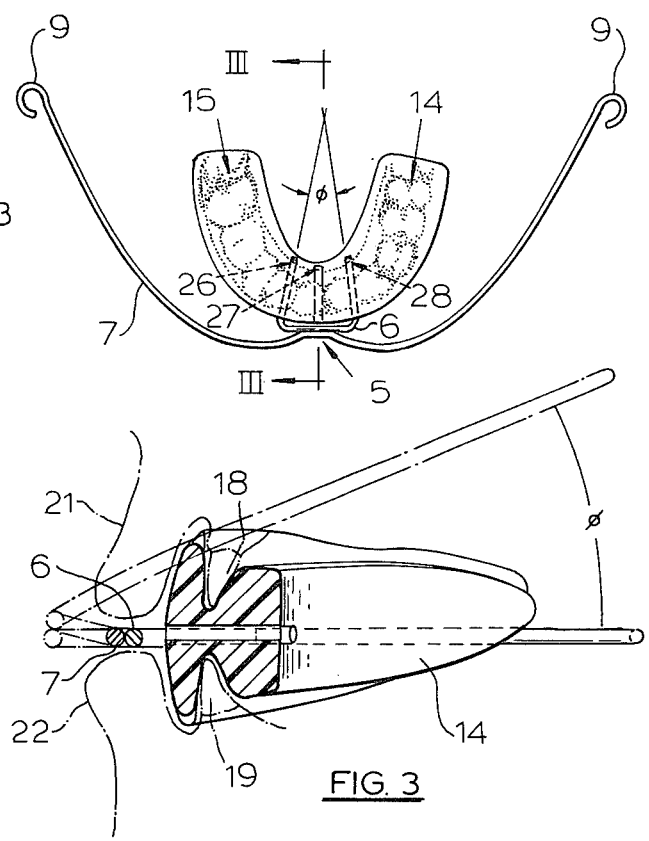
FIG. 2
FIG. 3
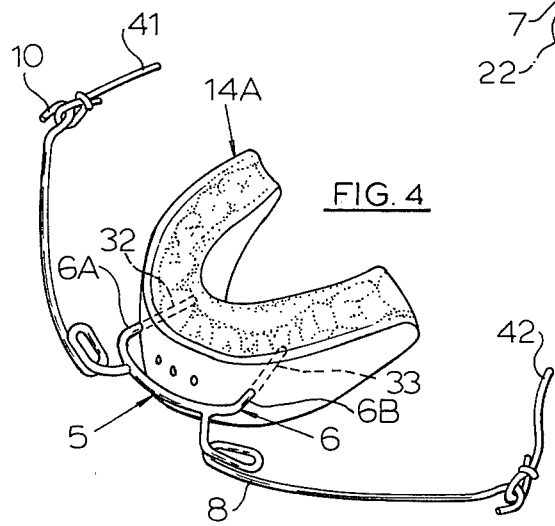
FIG. 4
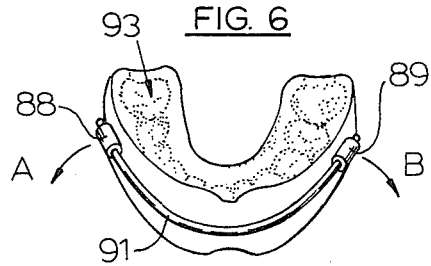
FIG. 6
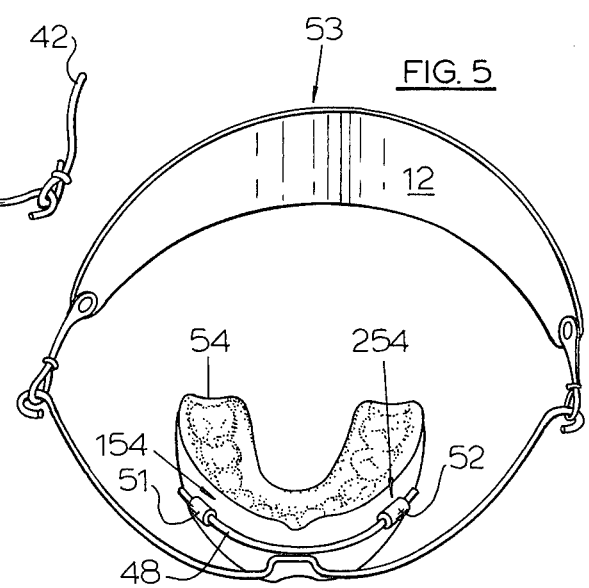
FIG. 5

MEANS FOR ATTACHING A HEADGEAR TO A POSITIONER

BACKGROUND OF THE INVENTION

1. Field of the Invention

The present invention relates to an orthodontic appliance, and more particularly to a means for attaching a headgear device to a tooth positioner, preformed or custom made.

2. Description of the Prior Art

In order to obtain movement of the teeth to effect an orthodontic treatment, it is necessary to allow a force to be applied to the teeth. Typically, bands on the individual teeth in conjunction with arch-wires have been used. However, this treatment requires the expenditure of a great deal of the practitioner's time and labor in addition to the disadvantages of having the apparatus firmly affixed in the patient's mouth for an extended period of time. Thus, there has been an increasing interest in the use of tooth positioner's both custom-made and preformed devices, (see my U.S. Pat. No. 3,898,736 regarding such preformed devices).

These positioning devices are adapted to be worn between the teeth of the upper and lower jaw, and are activated through the activity of masticatory, lingual, labial, and buccal muscles. Their correcting action depends to a great extent upon an accurate fit or engagement with the teeth. Prior to the preformed positioners, it was necessary to take accurate impressions of the patient's teeth and adjacent soft tissues, and to carefully fashion the appliance to fit the individual patient.

The headgear dental appliance was developed in part to avoid the fitting problems associated with these custom-made bands. These devices consisted of a mouthpiece formed of a resilient material having a curvature substantially conforming to the maxillary dental arch of a normal person. At the front, labial portion of the arch, either wires or a molded portion of the device would project from the arch, and out of the patient's mouth. When wire was utilized, the wire would be molded into the entire arch and become an integral part thereof. Where the projections were made from the resilient material, wires would be attached to them outside of the mouth. In either case, the wires arched rearwardly outside of the mouth, projecting out and curving around both sides of the face, to the attachment with an elastic band. This band was stretched around the back of the head or neck and connected both ends of the wire. The stretching force was transmitted to the wires, together creating a rearward force which was applied to the teeth. U.S. Pat. Nos. 2,822,612; 2,880,509, and 2,983,046 may be seen in this regard.

However, dentitions of individuals vary greatly among the population. This readily recognizable fact has resulted in a limitation to the extent of treatment available when utilizing the known devices. The mouthpiece portions were not designed to fit the teeth but only match the approximate shape of the arch. Additionally, the known devices are structurally formed into a unit, and are not practically separable—either structurally or therapeutically.

SUMMARY OF THE INVENTION

The present invention has, as an objective, providing a practical combination of the custom or preformed positioners with cervical or high pull headgear apparatus. As the positioners may also be used by themselves as a separate treatment or, perhaps more commonly, the headgear temporarily used to supplement or augment the positioner treatment, a simple yet effective way of combining the two treatments which readily permits a subsequent separation is desired.

These objectives are obtained by providing a number of alternative methods of attaching the wire portion of the headgear to the positioner. One method is to provide a pair of tubes having a diameter sufficient to receive the headgear wires. These tubes have portions which are selectively inserted into the desired position(s) on the positioner during the molding thereof or even after the molding has been completed by the use of an adhesive cement or by heating the wire and inserting it into the positioner. Depending upon the method of coupling the headgear with the positioner, a multitude of forms, a hook for example, can be attached to the positioner instead of the tubes.

In an alternate embodiment for the attachment, the headgear portion is provided with two ends for direct insertion into the positioner. These ends, parallel or non-parallel may be inserted directly into existing breathing holes, typically located in the front-labial portion, or they may be inserted into drilled holes which may be selectively drilled at the desired locations. Location on the side of the positioner would enable the headgear to assist with posterior movement of the entire dentition through its action against the positioner appliance.

Various other objects, advantages, and features of the present invention will become readily apparent from the ensuing detailed description and drawings, and the novel features will be particularly pointed out in the appended claims.

BRIEF DESCRIPTION OF THE DRAWINGS

FIG. 1 is a perspective view showing a headgear portion in use on a patient;

FIG. 2 is a plan view showing an embodiment of the combination headgear positioner;

FIG. 3 is a side sectional view in elevation taken along line III—III of FIG. 2;

FIG. 4 is a perspective view showing an embodiment of the combination;

FIG. 5 is a perspective view showing an alternate embodiment of the combination in its totality;

FIG. 6 is a perspective view showing an alternate use for an embodiment of the invention;

DESCRIPTION OF THE PREFERRED EMBODIMENTS

FIG. 1 shows an orthodontic patient with the headgear positioner combination in situ. As the positioner portion is inserted in the mouth during use, the only visible portions are parts of the headgear. Wires 1, 2 emerge from a patient's oral cavity and are bent rearwardly, each along one side of the face. The wires 1, 2 are connected to an elastic band 3, which is stretched across the cervix. The stretched band 3 pulls on both wires 1, 2 causing a force to be transmitted to the positioner.

Figure 16:
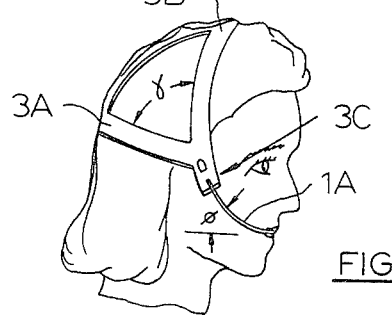
FIG. 16 is a side perspective view showing an alternate headgear portion in use on a patient.

An alternative to the cervical headgear shown in FIG. 1 is the high pull headgear shown in FIG. 16. Therein a pair of elastic bands 3A and 3B are provided and joined at junction 3C. The elastic bands 3A and 3B fit over the top and back portion of a patient's head forming an angle γ therebetween. Angle γ typically lies within the range of 10° to 170°. The bands 3A and 3B are connected to wire 1A at the junction 3C so that such force will be delivered to the positioner portion. Unlike the cervical headgear of FIG. 1, the wires 1A, 1A of this form of the invention are at an angle θ to the occlusal plane of the teeth. Angle θ is preferably 28°. The stretched bands 3A and 3B pull on wires 1A, 1A to cause both a rearward and upward force to be transmitted to the positioner.

One way of attaching the headgear portion to the positioner is illustrated in FIGS. 2-4. Attaching wire 6 is connected at 5 to a headgear wire 7. The wire 7 has end loops 9 for attachment to an elastic band 12 (FIG. 5). A positioner 14 of the type having a plurality of tooth impressions 15 is provided. The positioner 14 may be a custom-fitted positioner which is constructed after taking impressions of a particular patient. However, positioner 14 could also be a preformed positioner, such as the type disclosed in my U.S. Pat. No. 3,898,736. Additionally, positioner 14 could alternatively be an eruption guidance appliance of the type disclosed in my U.S. Pat. No. 4,139,944 i.e., an "Occlus-o-Guide", brand positioner, or a positioner of the type disclosed in my U.S. Pat. No. 4,073,061 entitled, "Closely Adapted Orthodontic Appliance". In any event, upper and lower teeth 18, 19 are received by the impressions 15 as shown in FIG. 3.

The positioner 14, in one embodiment of my invention, is connected to the headgear by the insertion of the attaching wire 6 into holes 26, 27, 28, which are typically provided in the positioner 14 to permit the patient to breathe through the mouth while the positioner 14 is in place. Attaching wire 6 is typically U-shaped, and thus forms two prongs 6A, 6B. The prongs 6A, 6B may be inserted into the breathing holes 26, 28 as in FIGS. 2 and 3 or, in an alternate embodiment, into separately formed holes 32, 33 (FIG. 4). A pair of holes 32, 33 may be formed during the molding of the positioner 14A, or they may be subsequently drilled therein.

Use of the holes 32, 33 permits the selection of various positions posterior of the breathing holes 26, 27, 28, which are usually placed in the anterior portion of the positioner 14. By such posterior placement, the headgear would be able to help with the posterior movement of the whole dentition by its action against the positioner appliance.

Regardless of the insertion points, the attachment wires 6 are connected to the outer wire 7 at the connection 5 anterior to the positioner 14 or 14A thereby permitting the outer wire 7 to project from the connection 5 and through the lips 21, 22.

The outer wire can be formed into different designs—having various loops and curvatures (see, for example, wire 8 in FIG. 4), the selection depending upon the treatment of the teeth desired. The different designs are located in close proximity to the mouth, and thereafter, the outer wires uniformly curve rearwardly along the face and towards the back of the head. A pair of loops 10, 11 are provided for the connection to the headgear wires 41, 42, which are in turn connected to an elastic band 12 (see FIGS. 4 and 5).

Figure 7:
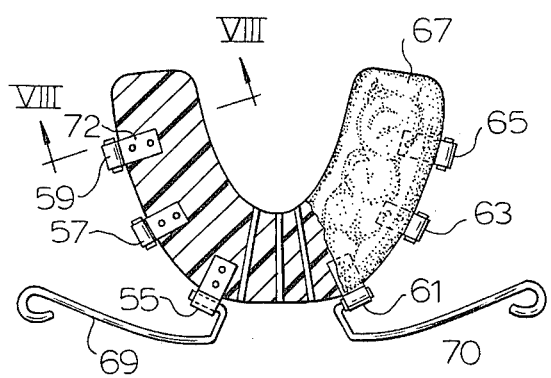
FIG. 7 is a plan view with portions cut away showing an embodiment of the invention.
Figure 8:
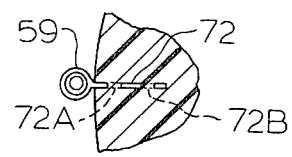
FIG. 8 is an elevational view in section taken along line VIII—VIII of FIG. 7.

FIGS. 5 and 7 illustrate an alternate way of attaching a headgear to a positioner. FIG. 5 shows the entire headgear-positioner apparatus, with a pair of tubes 51, 52 used to attach the headgear 53 to the positioner 54. The tubes 51, 52 are preferably made of stainless steel, a material which is relatively inert while in the mouth. The tubes 51, 52 may be of variable length and diameter, with a preferable size being 2-4 mm in length with an opening of 0.045 inch (1.14 mm). As shown in FIG. 7, the tubes 51, 52 can be placed at different lateral locations on the positioner. A plurality of cylindrical segments or tubes 55, 57, 59 and a corresponding plurality of symmetrical counterpart tubes 61, 63, 65 demonstrate posteriorly varying positions on a tooth positioner 67. A pair of wires 69, 70 is received by the tubes 55 and 61 (as shown), with the therapeutic effect varying as the location of the tubes 55-65 change. FIGS. 8-12 show these tubes 51, 52, and 55-65 in greater detail.

The tubes 51 and 52 are of variable diameter, such that the wire 48 attaching the headgear 53 to the positioner 54 may be safely received therein. A diameter of 0.045 inch proves compatible with most headgear apparatus. Each tube 51 and 52 is attached (soldered or welded) to a metal retention portion (not shown) which is inserted as at 154 and 254. The positioner is made out of a semi-resilient plastic or rubber material, and may be custom-fitted or selected from a set of preformed positioners, such as those disclosed in my U.S. Pat. No. 3,898,736. To further insure retention, the metal retention portion 72 of the tube 59 is provided with a pair of holes 72A, 72B.

Figure 9:
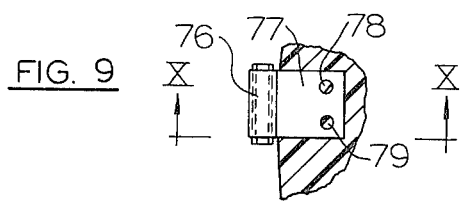
FIG. 9 is a partial plan view in section showing an anchoring device of the present invention.
Figure 10:
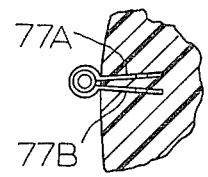
FIG. 10 is a side elevational view taken along line X—X of FIG. 9.
Figure 11:
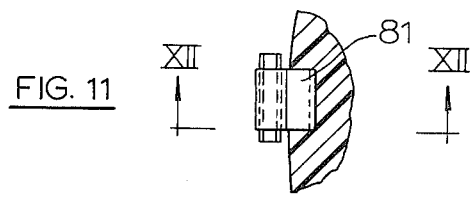
FIG. 11 is a view similar to FIG. 9 showing an alternate anchoring device.
Figure 12:
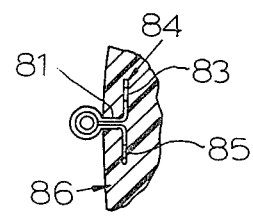
FIG. 12 is a side elevational view taken along line XII—XII of FIG. 11.

The use of the headgear 53 places a great deal of stress on the tube-positioner connection formed by the wire 48 and the tubes 51 and 52. To further insure retention, the metal retention portion (not shown in FIG. 5) may advantageously consist of a member of bent or flattened pieces. In FIG. 9, the tube 76 is connected to a flat metal retention portion 77 having a pair of holes 78, 79. As shown in FIG. 10, the metal retention portion 77 consists of a pair of angled flat pieces 77A and 77B, each having two holes 78 and 79. FIGS. 11 and 12 have a metal portion 81 consisting of two "L"-shaped pieces 83, 85, which form an inner surface 84 parallel to the outer surface 86.

Besides their use in attaching the headgear 53 to the positioner 54, the tubes 51 and 52 can be used to provide a different type of treatment for the dental arch. In FIG. 6, the tubes 88 and 89 are used in conjunction with an arch-wire 91. Depending upon the way the arch-wire 91 is formed, arch expansion or constriction may be obtained as its force is exerted on the teeth through the positioner appliance 93. In FIG. 6, this force is indicated by arrows A and B.

Figure 13:
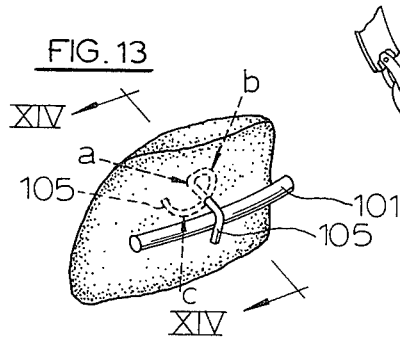
FIG. 13 is a partial side elevational view showing an alternate anchoring device.
Figure 14:
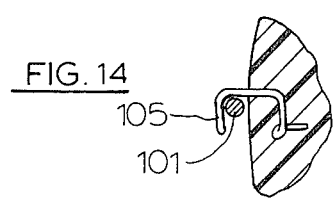
FIG. 14 is a partial side, sectional view in elevation taken along line XIV—XIV of FIG. 13.

Arch-wires can also be attached using a device other than tubes. In FIGS. 13 and 14 an embedded, bent wire is used to retain an arch-wire. In FIGS. 13 and 14, an arch-wire 101 is retained by embedded wire 105. The embedded wire may also be bent in other shapes, such as that shown by wire 106 in FIG. 15. The embedded portions of the wires 105 and 106 are given sufficient bends a, b, c, d, and e, to form an anchor which resists twisting in each direction besides being resistant towards being dislodged.

Figure 15:
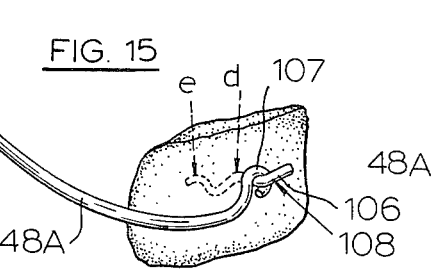
FIG. 15 is a view similar to FIG. 13 showing an alternate anchoring device.

The embedded wires 105 and 106 can also be used in conjunction with a high pull retainer. As shown in FIG. 15, a wire 48A, which is connected to the high pull headgear wire 1A, is provided with a loop 107 which engages with a hook 108 formed by the embedded wire 106. The upward force provided by the high pull headgear may thus be transferred to the positioner.

Regardless of the method of attachment to the positioner, it is contemplated, in accordance with my invention, that two sets of preferred headgear devices, which coordinate especially advantageously with preformed positioners constructed as disclosed in my U.S. Letters Patents, are utilized.

It is further contemplated that two separate sheets of headgear portions be provided in which the direction the force is applied to the positioner is varied in fulfillment of different therapeutic needs. A regular pull headgear is designed wherein the headgear wire 7 (FIG. 2), is horizontal, i.e., parallel to the occlusal plane of the teeth, when in use by a patient. There is additionally provided a high pull headgear appliance where the headgear wire 7 makes an angle $\theta$ with the occusal plane. This angle $\theta$ is preferably 28°.

Both the regular pull and high pull embodiments are provided in a small and regular size. In the small size, the prongs 6A, 6B have a length of 9 mm and form an angle $\phi$ of preferably 70°. The regular size has prongs 6A, 6B of 12 mm and an angle $\phi$ of 46°. (See FIGS. 2 and 4).

The small and regular sizes of both regular and high pull headgear are designed to be used with certain sizes of preformed positioners which are commercially available and are marketed under the trademark "ORTHO-TAIN" brand.

| SMALL SIZE — REGULAR AND HIGH PULL | | |
|---|---|---|
| FOUR BICUSPID EXTRACTION | NON-EXTRACTION | UPPER BICUSPID EXTRACTION |
| 1    X | 1    N | 2    U |
| 1½   X | 1½   N | 2½   U |
| 2    X | 2    N | 3    U |
|        | 2½   N | 3½   U |
|        | 3    N |        |
|        | 3½   N |        |

| REGULAR SIZE — REGULAR AND HIGH PULL | | |
|---|---|---|
| FOUR BICUSPID EXTRACTION | NON-EXTRACTION | UPPER BICUSPID EXTRACTION |
| 2½   X | 4    N | 4    U |
| 3    X | 4½   N | 4½   U |
| 3½   X | 5    N | 5    U |
| 4    X | 5½   N | 5½   U |
| 4½   x | 6    N | 6    U |
| 5    X | 6½   N |        |
| 5½   X | 7    N |        |
| 6    X |        |        |

While I have disclosed an exemplary structure to illustrate the principles of the invention, it should be understood that I wish to embody within the scope of the patent warranted hereon, all such modifications as reasonably and properly come within the scope of my contribution to the art.

I claim as my invention:

1. An improved orthodontic appliance of the type combining a resilient intraoral tooth positioner in arch form with a cervical headgear, wherein the improvement comprises:

means for a temporary attachment of the cervical headgear to the tooth positioner comprising:

anchoring means permanently affixed in the tooth positioner which comprises:

at least a pair of headgear tubes of a diameter capable of receiving headgear wires, and a metal retention portion attached to each of said tubes and together therewith forming said anchoring means and attached to form a firm anchor in the tooth positioner; and wire means for connection to the cervical headgear, said anchoring means and said wire means having detachable coupling means therebetween, whereby the cervical headgear may be selectively used during orthodontic treatment using the tooth positioner and the headgear tubes, which are firmly anchored to the tooth positioner via the attached metal retention portion thereof, receive the headgear wire means and transmit the force applied by the headgear to the tooth positioner.

2. An improved orthodontic appliance of the type combining a resilient intraoral tooth positioner in arch form with a cervical headgear, wherein the improvement comprises:

means for a temporary attachment of the cervical headgear to the tooth positioner comprising:

anchoring means permanently affixed in the tooth positioner, the tooth positioner having at least two breathing holes formed therein to provide said anchoring means; and wire means for connection to the cervical headgear, said wire means comprising an attaching wire, connected to the headgear and having two prongs, each received within one of said breathing holes, whereby the cervical headgear may be selectively used during orthodontic treatment using the tooth positioner.

3. An orthodontic appliance which allows therapeutic flexibility comprises:

a high pull headgear comprising:

a pair of elastic bands of a size sufficient to be stretched, one of said bands positioned around the back of a patient's head, the other of said bands positioned over the top of the head, and a junction connecting the pair of bands in a manner forming an angle between the bands during use by a patient;

a positioner of the type having a plurality of tooth impressions formed to receive the teeth of a patient; and a means for a temporary attachment of the high pull headgear to the tooth positioner comprising:

anchoring means permanently affixed in the tooth positioner which comprises:

at least a pair of headgear tubes of a diameter capable of receiving headgear wires, and a metal retention portion attached to each of said tubes and together therewith forming said anchoring means and attached to form a firm anchor in the tooth positioner; and wire means for connection to the high pull headgear, said wire means comprising a wire attached to and leading forwardly away from the junction, said anchoring means and said wire means having detachable coupling means therebetween;

whereby the upward force provided by the high pull headgear may be transferred to the positioner and to the teeth and the headgear may be selectively used during orthodontic treatment using the tooth positioner.

4. An orthodontic appliance as described in claim 3 wherein said positioner is a custom-made positioner.

5. An orthodontic appliance as described in claim 3 wherein said positioner is a preformed positioner.

6. An orthodontic appliance as described in claim 3 wherein the angle formed by said pair of elastic bands is between 10° and 170°.

7. An improved orthodontic appliance of the type combining a resilient intraoral tooth positioner in arch form with a cervical headgear, wherein the improvement comprises:

means for a temporary attachment of the cervical headgear to the tooth positioner are provided and comprise:

at least a pair of headgear tubes of a diameter capable of receiving headgear wires; and a metal retention plate having at least one perforation located therein attached to each of said tubes and attached to form a firm anchor in the tooth positioner, whereby the headgear tubes, which are firmly anchored to the tooth positioner via the attached metal retention plate portion thereof, receive the headgear wires and transmit the force applied by the headgear to the tooth positioner, and whereby the cervical headgear may be selectively used during orthodontic treatment using the tooth positioner.

8. An improved orthodontic appliance of the type combining a resilient intraoral tooth positioner in arch form with a cervical headgear, wherein the improvement comprises:

means for a temporary attachment of the cervical headgear to the tooth position are provided and comprise:

at least a pair of headgear tubes of a diameter capable of receiving headgear wires; and two metal retention plates each having at least one perforation therein, said retention plates vertically separated from one another forming an upper and lower retention plate, said plates attached to each of said tubes and attached to form a firm, anchor in the tooth positioner, whereby the headgear tubes, which are firmly anchored to the tooth positioner via the attached metal retention plate portion thereof, receive the headgear wires and transmit the force applied by the headgear to the tooth positioner, and whereby the cervical headgear may be selectively used during orthodontic treatment using the tooth positioner.

9. An improved orthodontic appliance of the type combining a resilient intraoral tooth positioner in arch form with a cervical headgear, wherein the improvement comprises:

means for a temporary attachment of the cervical headgear to the tooth positioner are provided and comprise:

at least a pair of headgear tubes of a diameter capable of receiving headgear wires; and two, L-shaped metal retention plates, each having at least one perforation therein, said L-shaped plates being arranged such that the two plates form a surface parallel to and beneath the surface of the tooth positioner, said plates attached to each of said tubes and attached to form a firm anchor in the tooth positioner, whereby the headgear tubes, which are firmly anchored to the tooth positioner via the attached metal retention plate portion thereof, receive the headgear wires and transmit the force applied by the headgear to the tooth positioner, and whereby the cervical headgear may be selectively used during orthodontic treatment using the tooth positioner.

10. An improved orthodontic appliance of the type combining a resilient intraoral tooth positioner in arch form with a cervical headgear, wherein the improvement comprises:

means for a temporary attachment of the cervical headgear to the tooth positioner are provided and comprise:

at least a pair of headgear tubes of a diameter capable of receiving headgear wires; and a metal retention plate portion attached to each of said tubes and attached to form a firm anchor in the tooth positioner, whereby the headgear tubes, which are firmly anchored to the tooth positioner via the attached metal retention plate portion thereof, receive the headgear wires and transmit the force applied by the headgear to the tooth positioner, and whereby the cervical headgear may be selectively used during orthodontic treatment using the tooth positioner.

* * * * *